US00PP34600P2

(12) United States Plant Patent
von Tubeuf

(10) Patent No.: US PP34,600 P2
(45) Date of Patent: Sep. 20, 2022

(54) POINSETTIA PLANT NAMED 'NPCW21350'

(50) Latin Name: *Euphorbia pulcherrima*
Varietal Denomination: NPCW21350

(71) Applicant: KLEMM + SOHN GMBH & CO. KG, Stuttgart (DE)

(72) Inventor: Guido von Tubeuf, Stuttgart (DE)

(73) Assignee: KLEMM+SOHN GMBH & CO. KG, Stuttgart (DE)

( * ) Notice: Subject to any disclaimer, the term of this patent is extended or adjusted under 35 U.S.C. 154(b) by 0 days.

(21) Appl. No.: 17/573,820

(22) Filed: Jan. 12, 2022

(51) Int. Cl.
*A01H 5/12* (2018.01)
*A01H 6/38* (2018.01)

(52) U.S. Cl.
USPC ..... Plt./303

(58) Field of Classification Search
USPC ..... Plt./302, 303
See application file for complete search history.

(56) References Cited

PUBLICATIONS

YouTube.com/watch?v=2o40xn-KSR0, New Orange Glow Poinsettia—N.G. Heimos Greenhouses Dec. 3, 2020. Retrieved from the Internet on Mar. 1, 2022.*
ballseed.com/PlantInfo/?phid=; 'Orange Glow' Poinsettia—Plant Information (Retrieved from the Internet on Mar. 2, 2022).*

* cited by examiner

*Primary Examiner* — Susan McCormick Ewoldt
(74) *Attorney, Agent, or Firm* — Weatherly IP Solutions, LLC; James M. Weatherly

(57) ABSTRACT

A new poinsettia plant particularly distinguished by having a medium-high vigor, 60 day response time, and obtuse leaf shape, is disclosed.

1 Drawing Sheet

Genus and species: *Euphorbia pulcherrima.*
Variety denomination: 'NPCW21350'.

BACKGROUND OF THE NEW PLANT

The present invention comprises a new and distinct variety of poinsettia, botanically known as *Euphorbia pulcherrima* and hereinafter referred to by the variety name 'NPCW21350'. 'NPCW21350' is a selection from a cross-pollination conducted in December 2015 in Nairobi, Kenya of the proprietary female *Euphorbia* line 'EP-2013-0217' (unpatented) and the proprietary male *Euphorbia* line 'EP-2013-1229' (unpatented) in Nairobi, Kenya. Seeds from the cross were selected and plants were grown for evaluation. A plant line was selected in October 2016 in Stuttgart, Germany and named 'NPCW21350'. In May 2017, 'NPCW21350' was first vegetatively propagated by apical cuttings. 'NPCW21350' was found to reproduce true to type in successive generations of asexual propagation via apical cuttings in Stuttgart, Germany.

SUMMARY

The following are the most outstanding and distinguishing characteristics of this new variety when grown under normal horticultural practices in Stuttgart, Germany.

1. Medium-high vigor;
2. 60 day response time; and
3. Obtuse leaf shape.

DESCRIPTION OF THE PHOTOGRAPH

This new poinsettia plant is illustrated by the accompanying photograph which shows an overall view of the plant.

The photograph is of a plant approximately thirteen-weeks-old, grown indoors Stuttgart, Germany in December 2019. The colors shown are as true as can be reasonably obtained by conventional photographic procedures.

DESCRIPTION OF THE NEW VARIETY

The following detailed descriptions set forth the distinctive characteristics of 'NPCW21350'. The data which define these characteristics were collected from asexual reproductions carried out in Stuttgart, Germany. Data was collected on thirteen week old plants grown indoors in Stuttgart, Germany under greenhouse conditions in December of 2021. Color references are to The R.H.S. Colour Chart of The Royal Horticultural Society of London (R.H.S.), 5$^{th}$ edition (2007).

Classification:
- *Family.*—Euphorbiaceae.
- *Species.*—*Euphorbia pulcherrima.*
- *Common name.*—Poinsettia.
- *Variety.*—'NPCW21350'.

Parentage:
- *Male.*—*Euphorbia* line 'EP-2013-1229' (unpatented).
- *Female.*—*Euphorbia* line 'EP-2013-0217' (unpatented).

Plant:
- *Form.*—Triangular.
- *Growth habit.*—Upright.
- *Height.*—27.0 cm to 30.0 cm.
- *Width.*—35.0 cm to 38.0 cm.
- *Average number of inflorescences per plant.*—4.5.
- *Keeping quality.*—Good.
- *Time to produce a cutting.*—5 weeks.

*Blooming habit*.—Intermittent.
*Flowering response time*.—60 days.

Propagation:
*Type cuttings*.—Apical cuttings.
*Time to produce a rooted cutting*.—4 weeks.
*Rooting habit and root color*.—Freely branching and white.

Lateral branches:
*Color*.—RHS 137D.
*Length*.—20.0 cm to 23.0 cm.
*Internode length*.—1.0 cm to 3.0 cm.
*Diameter*.—0.4 cm to 0.8 cm.
*Branching habit*.—Freely branching.
*Number of lateral branches per plant*.—4 to 5.
*Texture*.—Smooth.
*Strength*.—Medium.

Leaves:
*Quantity*.—5 per lateral branch.
*Arrangement*.—Alternate.
*Number of lobes on the leaf blade*.—2.
*Lobation depth*.—Shallow.
*Depth of the deepest sinus of the leaf blade*.—0.6 cm.
*Shape*.—Obtuse.
*Apex*.—Acuminate.
*Base*.—Rounded.
*Margin*.—Almost entire.
*Length*.—8.0 cm to 12.0 cm.
*Width*.—6.0 cm to 8.0 cm.
*Texture*.—Upper surface: Smooth. Lower surface: Pubescent.
*Vein color*.—Upper surface: Transparent. Lower surface: RHS 139D.
*Variegation*.—Absent.
*Venation pattern*.—Reticulate.
*Color*.—Mature foliage: Upper surface: Closest to RHS 139A. Lower surface: RHS N138B. Immature foliage: Upper surface: RHS 139A. Lower surface: RHS 137C.
*Leaf petiole*.—Length: 3.0 cm to 6.0 cm. Diameter: 0.2 cm to 0.4 cm. Color: Upper (part) surface: Greenish with transition to RHS 34B. Lower (part) surface: RHS 139D. Texture: Smooth. Strength: Medium. Transitional leaves: Sparse. Shape: Obtuse. Length: 6.0 cm to 9.0 cm. Width: 4.0 cm to 5.0 cm. Color: Upper surface: RHS 139A and RHS N30A. Lower surface: RHS 137C and RHS N30A.

Inflorescence:
*Type and habit*.—Cluster of cyathia surrounded by bracts.
*Quantity per lateral branch*.—1.
*Position relative to foliar plane*.—Above.
*Lastingness of inflorescence on the plant*.—4 to 5 weeks.
*Natural flowering season*.—November.
*Diameter*.—20.0 cm to 23.0 cm.
*Height*.—2.0 cm to 3.0 cm.
*Fragrance*.—Absent.

Bracts:
*Number of bracts per inflorescence*.—10 to 12.
*Shape*.—Obtuse.
*Apex*.—Acuminate.
*Base*.—Rounded.
*Margin*.—Almost entire.
*Size*.—Length: 12.0 cm to 15.0 cm. Width: 5.0 cm to 7.0 cm.
*Texture (both upper and lower surfaces)*.—Smooth.
*Folding along the main vein*.—Absent.
*Twisting*.—Absent.
*Rugosity between the veins*.—Weak.
*Venation pattern*.—Reticulate.
*Vein color*.—Upper surface: RHS N34A. Lower surface: Closest to RHS 31C but weaker.
*Bract color*.—Upper surface: Closest to RHS N30A. Lower surface: Closest to RHS 41A.
*Bract petiole*.—Length: 1.0 cm to 1.8 cm. Diameter: 0.2 cm. Color: Upper (part) surface: Closest to RHS 34A. Lower (part) surface: Closest to RHS 31C. Texture: Smooth. Strength: Medium.

Cyme:
*Diameter*.—1.0 cm to 2.0 cm.
*Cyathia number*.—3.0 cm to 5.0 cm per inflorescence.
*Deformation of glands of the cyathium*.—Absent.
*Timing of opening of cyathia*.—Opens end of November; first pollen appears in parallel to opening of the nectar cups, stigmas appear 2 weeks later.
*Cyathium*.—Shape: Ovate. Texture: Smooth. Diameter: 0.3 cm to 0.6 cm. Length: 0.4 cm to 0.7 cm. Color: RHS 142B.
*Peduncle*.—Color: RHS 142B. Length: 0.2 cm. Diameter: 0.1 cm. Texture: Smooth. Strength: Medium.
*Nectar cups*.—Number: 1 per cyathium. Diameter: 0.1 cm. Length: 0.2 cm to 0.3 cm. Color: RHS N30B (upper lip) and RHS 17C (lower lip). Shape: Lip shaped. Texture: Smooth.

Reproductive organs: Stamen quantity: 10-15 per cyathium.
*Stamen shape*.—Ovate.
*Filament length*.—0.4 cm to 0.5 cm.
*Filament color*.—RHS 44C.
*Pollen quantity*.—Sparse.
*Pollen color*.—Not visible.
*Gynoecium*.—Not visible.

Fruit and seed set: Not observed.

Disease and insect resistance: No particular disease or insect resistance observed.

COMPARISON WITH PARENTAL LINE AND KNOWN VARIETY

'NPCW21350' is distinguished from its mutation parent as described in Table 1:

TABLE 1

| Comparison with Parental Lines | | | |
|---|---|---|---|
| Trait or characteristic | Instant variety 'NPCW21350' | Female parent 'EP-2013-0217' | Male Parent 'EP-2013-1229' |
| Vigour | Medium-high | Low | Compact-medium |
| Response time | 60 days | 65 days | 56 days |

COMPARISON WITH SIMILAR VARIETY

'NPCW21350' is most similar to the commercial poinsettia plant named 'Orange Spice' (patent status unknown). Differences between the two varieties are described in Table 2:

TABLE 2

| Trait | Variety 'NPCW21350' | Commercial line 'Orange Spice' |
|---|---|---|
| Response time | 60 days | More than 65 days |
| Leaf shape | Obtuse | More lanceolate |

I claim:

1. A new and distinct cultivar of Poinsettia Plant Named 'NPCW21350' as described and illustrated herein.

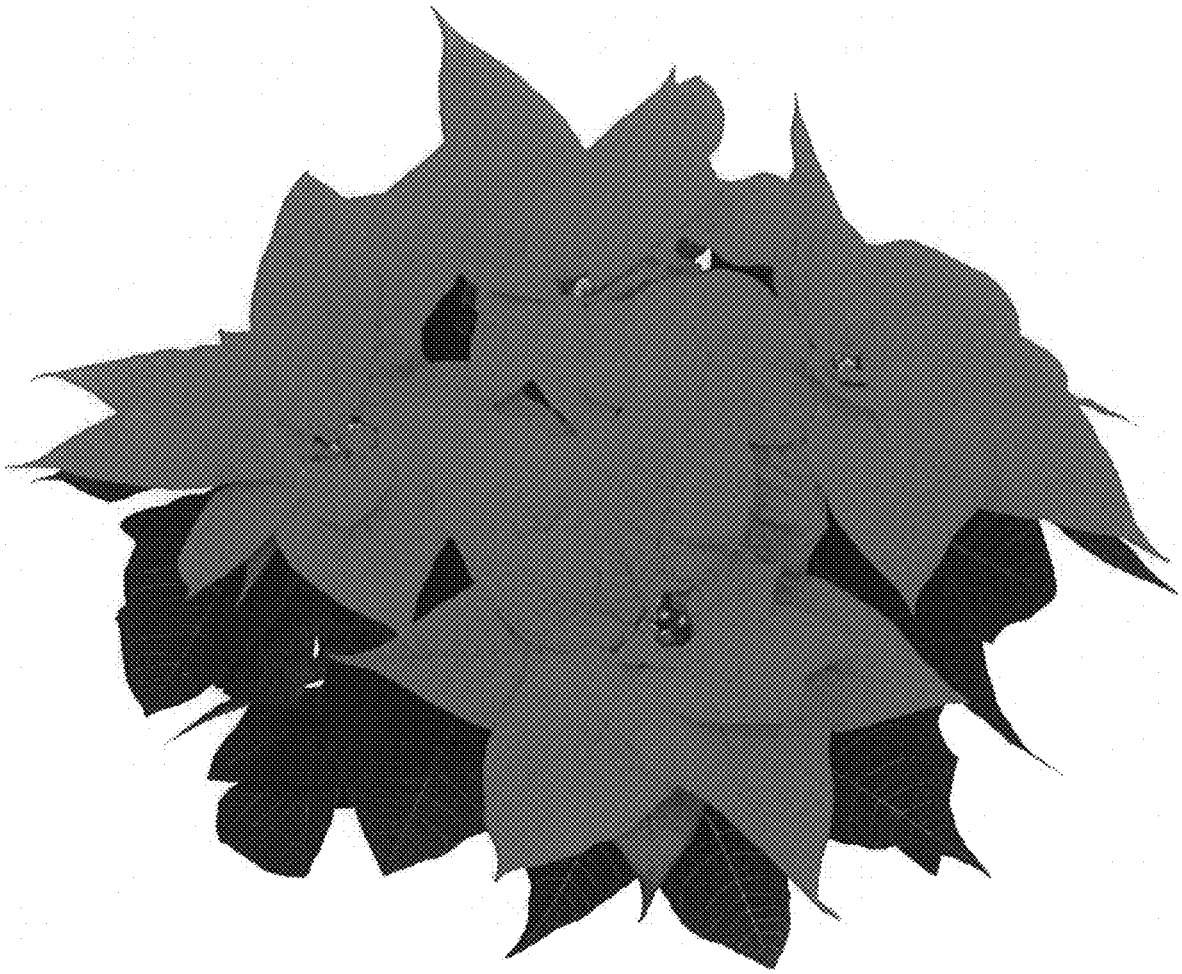

* * * * *